United States Patent [19]

Brown et al.

[11] Patent Number: 5,151,451
[45] Date of Patent: Sep. 29, 1992

[54] TRANSLUCENT, THIXOTROPIC HYGEL

[75] Inventors: Charles R. Brown, Bedford; Peter Wilding, Wellingborough, both of Great Britain

[73] Assignee: Van den Bergh Foods Co., Division of Conopco, Inc., Lisle, Ill.

[21] Appl. No.: 706,819

[22] Filed: May 29, 1991

[30] Foreign Application Priority Data

May 29, 1990 [GB] United Kingdom ............... 90201357

[51] Int. Cl.$^5$ .......................... A23J 3/00; B01J 13/00; A61K 47/42
[52] U.S. Cl. .................................. 514/773; 252/315.1; 424/1; 426/573; 426/602; 426/605; 514/944
[58] Field of Search .................... 252/315.1; 424/401; 426/602, 605, 573; 514/773, 944

[56] References Cited

U.S. PATENT DOCUMENTS 4,209,503  6/1980  Shah et al. ............................ 424/49
4,548,736  10/1985  Müller et al. ..................... 252/315.1

FOREIGN PATENT DOCUMENTS 0012485  6/1980  European Pat. Off. .
0129346  12/1984  European Pat. Off. .
0323529  7/1989  European Pat. Off. .
0347237  12/1989  European Pat. Off. .
0352144  1/1990  European Pat. Off. .
0355058  2/1990  European Pat. Off. .
0356094  2/1990  European Pat. Off. .
0412590  2/1990  European Pat. Off. .
0369550  5/1990  European Pat. Off. .
0250623  10/1990  European Pat. Off. .
2063273  6/1981  United Kingdom .

OTHER PUBLICATIONS

WP 89/05587.
EP Search Report 90 20 1357 EP 12,485 (Abstract).

Primary Examiner—Richard D. Lovering
Assistant Examiner—N. Bhat
Attorney, Agent, or Firm—Gerard J. McGowan, Jr.

[57] ABSTRACT

The invention concerns with translucent, thixotropic non-particulate denatured protein containing aqueous gels. Also a process for the preparation of these gels is disclosed. The gels can be incorporated in food products and in cosmetics.

31 Claims, No Drawings

TRANSLUCENT, THIXOTROPIC HYGEL

So far in literature denatured protein containing compositions, as well as their preparation and their application in food products have been mentioned. In fact these compositions can be split up into two groups of compositions, one group (Labatt) consists of compositions of non-aggregated, denatured protein particles which must have a particle size of 0.1-2.0 um in order to have emulsion-like organoleptic character and which are made by processes in which a heat treatment is carried out while using a high shear (see EP 250623, EP 323529 and WO 89/05587). Another group (Unilever) consists of compositions of non-aggregated, denatured protein particles, which possess a particle size of 0.1-20 um and which still have an emulsion-like organoleptic character. These particles are made by carrying out a heat treatment with high shear or by carrying out a heat treatment using hardly any shear, and in which the pH is adjusted to a special value. (See EP 347237, EP 352144, EP 355058, EP 356094, EP 369,550, GB 8918276.0 and EP 902000.1).

Denatured protein containing gels are also known in the literature. E.g. EP 129,346 discloses a food product base that is obtained by a process in which a whey protein containing concentrate (max. 7.5 wt% of protein) is heated until a gel is formed with a non-grainy texture. According to the specification (see page 4, lines 18-29 and the examples) always an oil is present in the composition that is heated. Moreover it is explicitely stated that shear cannot be applied in the process, because this will lead to a breaking of the gel (page 7, lines 27-31).

According to GB 2,063,273 a composition of a soluble, denatured whey protein is prepared by heating an aqueous solution of native whey with a pH of at least 6.5. The protein concentration of this solution is maximum 5 wt%, i.e. below the critical gel concentration of whey protein. After the heating the solution is cooled and the pH is adjusted to 4-5, whereupon the composition is centrifugated. The precipitate is redissolved in water by neutralisation until pH >6.5.

Therefore above literature does not disclose the preparation of thixotropic, non-particulate denatured protein containing aqueous gels.

We now have found compositions of denatured proteins that possess surprising properties, because aqueous compositions of these particles are translucent and thixotropic.

In the context of this patent the term thixotropy refers to a loss of gel character on the application of shear, a decrease in viscosity with increasing shear, followed by a gradual recovery of viscosity and gel character when the shear is stopped.

So our invention in the first place is concerned with translucent, thixotropic aqueous gels containing non-particulate denatured protein. The protein in the gel can be fully denatured, but in general it still consists partly of undenatured protein.

The gels contain protein in concentrations above the critical gel concentration for the protein, preferably 1.5-b 2.5 times the critical gel concentration.

The gels can contain (denatured) protein in concentrations up to 50 wt.%, preferably 1-40 wt%, most preferably 5-20 wt.%.

The denatured protein in these gels can be derived from every kind of protein source, e.g. whey protein, milk protein, bovine protein, egg-protein, animal, soluble fibrous proteins, e.g. from the myosin muscles, but also vegetable protein like soy-protein. Preferred protein-sources are whey protein and storage protein, especially soy-protein.

The gels according to the invention do not contain a detectable amount of particles (using light microscopy with a magnification of about 1000x) or by the preferred particle size determination methodology described in patent EP 323,529. Therefore with few particles to scatter light these gels appear translucent.

In order to avoid protein aggregation it is necessary that divalent cations, in particular $Ca^{2+}$, are absent.

The gels according to the invention, when measured by small deformation oscillatory techniques, using equipment such as a Bohlin rheometer, display viscoelastic character typical of gel materials, and can possess at 10° C. a complex modulus of 50 Pa to 100 KPa, in particular of 250 Pa -10 KPa, comprising an elastic modulus of 500 Pa and a loss modulus of 50 Pa, when measured on gels with 8 wt% protein. On the application of shear the gels according to the invention can possess at 10° C. a viscosity of less than 10 Pa s after shearing at 20-100 $S^{-1}$ for 100-500 sec, in particular of 3 Pa s when measured at a shear rate of 46.5 $sec^{-1}$ and after shearing for 200 sec.

The gels according to the invention may also be characterized by measuring the absorption or transmission of light by the gel. When an absorption spectrum is made (using a spectrophotometer such as a Pye Unicam SP8-200 and a sample pathlength of 1 mm), away from the wavelengths at which the protein components absorb, the value of light transmission is 5 to 50 percent.

The invention is also concerned with a process for the preparation of the above-mentioned translucent, thixotropic, non-particulate denatured protein containing aqueous gel which is characterized by making an aqueous solution of a water soluble protein with a protein concentration above the critical gel concentration for the protein, that contains no or small detectable amounts of dispersed solid particles and heating this solution under a shear of at least 1000 $S^{-1}$ at a temperature of 60-150° C.

In this way a gel is obtained after resting and cooling to room temperature, which is translucent and thixotropic and which cannot be removed from the reaction vessel without stirring it first. The best results are obtained, when the protein concentration of the aqueous protein solution is 1.5-2.5 times its critical gel concentration.

Alternatively the mixture may be cooled whilst still applying shear, producing a translucent liquid which subsequently gels on resting.

The preferred heating temperature is 80-130° C., whereas the shear used is preferably more than 8000 $S^{-1}$, most preferably more than 20.000 $S^{-1}$.

The proteins used in this process are the proteins mentioned above, preferably whey and Soy-protein. This protein can be completely soluble in water, in which case the starting solution is obtained immediately. However the protein solution can also be made from protein sources, which are only partly soluble in water. In this case the insolubles must be removed from the solution before the heating is carried out. This removal can be achieved in every known way e.g. by filtration or by centrifugation etc.

Another way of obtaining a protein solution is by making a protein dispersion in water and adding a salt, derived from a monocation, to the dispersion.

Whilst the preferred product is made from protein solutions containing no detectable particles, a product with the desirable thixotropic character can also be made from protein solutions containing substantial amounts of particles. However, products made from such material show reduced translucency.

The invention also concerns food products, which contain gels made according to the invention. Food products, that might contain these gels are spreads, creams, ice-creams, dressing, mayonnaise, soft cheese, yoghurt, etc.

The gels can be used in these products either to replace part of the fat of the product, or as gelling agents. So e.g. a spread can be made, which comprises an emulsion of water and oil, in which an appropriate amount of the gel according to the invention is incorporated. The gels can also be used for the stabilization of foams, obtained after aeration of food products, e.g. non-dairy creams or ice-creams.

The invention also concerns non-food products such as cosmetics which contain gels made according to the invention. In this case the gel can be used as an aid to spreading the cosmetic product on the skin. The gel can also be used as a base for microbiological growth support.

The invention will be further illustrated with the aid of the following examples:

EXAMPLE I

Low lactose, low fat, deionised (calcium free) whey protein (Quest International, Zwijndrecht, Holland) was dissolved in deionised water (<25 ohm/ml) at room temperature using a Silverson mixer on its lowest speed setting. To the solution was added Potassium Sorbate (0.2% w/w), Sodium Chloride (1% w/w), (optional) and lactic acid to bring the pH to 6.0. If necessary, the solution was next clarified by centrifugation at >10000 $\times$g for 20 min and 25° C.

A process line was assembled comprising a feed tank fitted with jacket, baffles and stirrer connected to a gear pump using 6 mm internal diameter high pressure plastic tubing. The gear pump was connected in like manner to a high speed churn (Unilever Research BV, T.A.U., Olivier van Noortlaan 120, Vlaardingen, Holland). This equipment comprised a jacketed, cylindrical barrel with a smooth internal surface fitted with a smooth surfaced rotor and having an annular gap of 2 mm. The high speed churn (HSC) was connected directly (without the use of tubing) to a scraped surface heat exchanger (A-Unit) (Heynau, Moosacher Strasse 51, Munich 40, Germany). The high speed churn jacket was connected to a water bath maintained at 98° C. while the A-Unit jacket was connected to a refrigerated bath with coolant held at 10° C. Clarified whey protein solution (12% w/w protein) was placed into the feed tank and warmed to between 35° C. and 45° C. (jacket temperature of 45° C). The units were energized such that the HSC operated initially at 1000 r.p.m. without any heating applied to the jacket. The A-Unit was run at 1000 r.p.m., generating a displacement shear rate of about 12000 s$^{-1}$, with coolant flowing through the jacket. The gear pump speed was set to give an output from the process line of about 50 g/min. When protein was allowed to flow through the process line. When it emerged from the final A-unit heating was applied to the high speed churn and its rotor speed increased to 5000 r.p.m., giving a displacement shear rate of about 5600 s$^{-1}$.

As a result, a product was collected at 20 +/−2° C., comprising a thixotropic, translucent stream of denatured liquid whey protein which possessed the following typical properties:

| | |
|---|---|
| Complex modulus at 10° C. (G*) ranging | 250–10000 Pa |
| Viscosity at 10° C. (Couette flow/ Bohlin VOR) after 200 s at 46.5 s$^{-1}$ of | 3.0 Pas |
| Light transmission at 1 mm path length and 600 nm of | 40% |

EXAMPLE 2

A solution of soya protein was made by dispersing 3 kg of soya concentrate ("Newpro", T Lucas Ingredients Ltd., Bristol, England) in 30 litres of deionised water containing 30 g potassium sorbate as an antimicrobial agent. The dispersion of flour was achieved by mixing dry ingredients with water using a Silverson mixer/ emulsifier operated at maximum speed. When the concentrate was adequately dispersed mixing was continued for another 20 min. to ensure maximum dissolution of the soya proteins. Sodium chloride was added (0.2% w/w) and lactic acid added to set the dispersion pH to 6.0. Insoluble material was then removed from the dispersion by centrifugation at 10000 $\times$g for 30 min. Clarified extract was decanted and residual pigments and off-flavours removed by subjecting the extract to a threefold concentration and dilution cycle. Salt solution was removed using an ultrafiltration (UF) plant having a membrane cut-off value of 30000 Dalton and sodium chloride solution (0.2% w/w) in tap water used to dilute the UF retentate.

Soya protein concentrate (10% w/w protein) was processed through the apparatus described in Example 1 to produce a translucent gel with thixotropic character.

EXAMPLE 3

A low fat spread comprising 10% w/w fat phase was prepared as follows: 90% of translucent, thixotropic viscous aqueous phase, having the composition set out below was mixed with a fat blend containing 2% w/w of saturated mono-glycerides (Hymono 4404). The fat blend was composed of:

| | Parts (on phase) |
|---|---|
| Rapeseed oil | 44.1 |
| Rape 32 oil | 34.3 |
| Palm oil | 19.6 |
| Butter flavour (Edlong) | 1.9 |
| Beta carotene | 0.002 |
| Aqueous phase | |
| Whey protein isolate (calcium free) | 15 |
| Potassium Sorbate | 0.2 |
| Sodium chloride | 1 |
| Deionised water | 83.8 |

The aqueous phase was processed by the method described in Example 1 and the output from the final A-unit connected to one end of a high speed crystalliser (HC-Unit) (Heynau, Moosacher Strasse 51, Munich 40, Germany). Fat phase was preheated to 45° C. in a stirred feed tank and fed via a piston pump (MPL Pumps Ltd., Feltham, Middlesex, England) into the HC-Unit through a centrally located port. The unit was energized and operated at 4000 r.p.m. with the jacket coolant applied at 10° C. A water continuous low fat product with the smooth spreading qualities reminiscent of a fat spreads with 25 to 40% fat was collected from the output port of the HC-Unit.

EXAMPLE 4

A hand cream was prepared from a vegetable oil and an aqueous protein preparation made by the method of Example 1. Aqueous phase (50%) having the composition given below was combined with oil phase (50%) containing emulsifier and perfume. The oil blend was as follows:

|  | Parts (on phase) |
|---|---|
| Sunflower oil | 88.6 |
| Hymono 7804 (Quest International) | 7.2 |
| Camellia oil | 4 |
| Perfume SC 1926 (Quest International) | 0.2 |
| Aqueous phase | |
| Whey protein isolate (Calcium free) | 13.5 |
| Potassium Sorbate | 0.2 |
| Deionised water | 86.3 |

A pourable aqueous phase was prepared by the method of Example 1 and loaded into a batch scraped surface heat exchanger (mixer unit) with a torque meter fitted to the drive shaft. Two water baths, one containing hot water (75° C.) and the other containing cold water (20° C.), were connected to the jacket of the mixer unit via a two way valve. The mixer unit was energized and operated at a rotor speed of 400 r.p.m. and hot water applied to the jacket. The temperature of the aqueous phase was raised to 75° C. whereupon oil phase, preheated to 75° C., was added to the aqueous phase. When all the oil had been added the mixer unit rotor speed was increased to 1000 r.p.m. and maintained at this speed for 2 min. The jacket temperature of the mixer unit was lowered by switching to cold water feed and upon inversion of the emulsion, the rotor speed was lowered to 400 r.p.m. and operated at this speed while the emulsion was cooled to 22° C. The torque applied by the mixer unit motor was used to monitor phase inversion from o/w to w/o. A smooth oil continuous hand cream resulted which exhibited thixotropic character when applied to the skin.

We claim:

1. Translucent, thixotropic, non-particulate denatured protein containing aqueous gel.

2. Translucent, thixotropic non-particulate protein containing aqueous gel according to claim 1, in which a substantial amount of the protein is denatured.

3. Thixotropic aqueous protein gel according to claim 1 comprising mainly of denatured protein, and containing some undenatured protein.

4. Gel according to claim 1, wherein the protein concentration is above the critical gel concentration for the protein.

5. Gel according to claim 4, wherein the protein concentration is 1.5-2.5 times the critical gel concentration for the protein.

6. Gel according to claim 1, wherein the protein concentration is 1-40 wt%.

7. Gel according to claim 1, wherein the protein concentration is 5-20 wt%.

8. Gel according to claim 1, wherein the protein is derived from whey.

9. Gel according to claim 1, wherein the protein is a storage protein.

10. Gel according to claim 9, wherein the protein is derived from soy beans or soy-seeds.

11. Gel according to claim 1, wherein the protein is an animal, soluble, fibrous protein.

12. Gel according to claim 1, wherein the gel contain few particles, which are detectable under a microscope, using a magnitude of $1000\times$.

13. Gel according to claim 1, wherein the complex modulus of the gel at 10° C. is 50Pa to 100kPa.

14. Gel according to claim 13, wherein the complex modulus of the gel at 10° C. is 250Pa-10KPa.

15. Gel according to claim 1, wherein the viscosity of the gel at 10° C., after shearing at 20 to 100 $S^{-1}$ for 100 to 500 sec is less than 10 Pa.s.

16. Gel according to claim 1, wherein the light transmission varies between 5 and 50% when measured at a pathlength of 1 mm at wavelengths where the absorption of the protein components is low.

17. Process for the preparation of a translucent, thixotropic, non-particulated denatured protein containing gaseous gel by making an aqueous solution of a water soluble protein with a protein concentration above the critical gel concentration for the protein, that contains no or small detectable amounts of dispersed solid particles and heating this solution under a shear of at least 1.000 $S^{-1}$ at a temperature of 60-150° C., whereas the shear optionally is maintained during cooling of the gel.

18. Process according to claim 17, wherein the protein concentration of the aqueous protein solution is 1.5-2.5 times the critical gel concentration.

19. Process according to claim 17, wherein the solution is heated at a temperature of 80-130° C.

20. Process according to claim 17, wherein the solution is heated under a shear of more than 8.000 $S^{-1}$.

21. Process according to claim 20, wherein the solution is heated under a shear of more than 20.000 $S^{-1}$.

22. Process according to claim 17, wherein the protein containing solution is obtained from whey.

23. Process according to claim 17, wherein the protein containing solution is obtained from storage protein, in particular soy-protein.

24. Process according to claim 17, wherein the protein containing solution is obtained by dissolving the water soluble part of a partly in water soluble protein in water and removing the unsolved particles.

25. Process according to claim 17, wherein the protein solution is obtained by dispersing a protein in water and dissolving the dispersed protein by the addition of a monovalent salt.

26. Process according to claim 17, wherein the protein containing solution has a protein-concentration of 1-40 wt.%.

27. Process according to claim 17, wherein the protein feedstock contains particulate material.

28. Food products containing the gel of the claim 1.

29. Process for the preparation of a spread with an oil continuous or a water continuous phase by making an emulsion of the required fat and water and incorporating the thixotropic gel of claim 1.

30. Cosmetic products containing the gel of claim 1.

31. Food product of claim 2, wherein the food product is selected from the group consisting of spreads, creams, ice-cream, dressings, mayonnaise, cheese, soft cheese and yoghurt.

* * * * *